United States Patent [19]

Vanlerberghe et al.

[11] 4,058,629
[45] Nov. 15, 1977

[54] POLYHYDROXYL MONOSULFOXIDE SHAMPOO COMPOSITIONS

[75] Inventors: Guy Vanlerberghe, Montjay-la-Tour; Henri Sebag, Paris, both of France

[73] Assignee: L'Oreal, Paris, France

[21] Appl. No.: 703,667

[22] Filed: July 8, 1976

Related U.S. Application Data

[60] Division of Ser. No. 563,459, March 31, 1975, Pat. No. 3,984,480, Continuation of Ser. No. 372,103, June 21, 1973, abandoned, which is a continuation-in-part of Ser. No. 142,410, May 11, 1971, abandoned.

[30] Foreign Application Priority Data

May 12, 1970 Luxembourg ............................ 60899

[51] Int. Cl.$^2$ .................... A61K 7/50; C11D 1/755
[52] U.S. Cl. ...................................... 424/365; 8/10.2; 8/11; 252/549; 252/352; 252/353; 424/70
[58] Field of Search ................ 252/549, 352, 353; 424/70, 365

[56] References Cited

U.S. PATENT DOCUMENTS

| | | | |
|---|---|---|---|
| 2,864,866 | 12/1958 | Louthan | 260/607 D X |
| 3,382,180 | 5/1968 | Priestly et al. | 260/607 AL |
| 3,522,311 | 7/1970 | Hickner | 260/607 AL |

FOREIGN PATENT DOCUMENTS

| | | | |
|---|---|---|---|
| 2,022,576 | 10/1972 | France | 260/607 A |
| 1,500,525 | 10/1966 | France | 260/607 A |
| 56,98M | 1/1968 | France | 260/607 A |
| 1,080,199 | 12/1963 | United Kingdom | 260/607 A |

OTHER PUBLICATIONS

"Hydroxyalkylsulfoxide" by Dr. H. Distler, Fette Seifen, Anstrichmettel, 70, pp. 21–23.

Primary Examiner—Delbert R. Phillips
Attorney, Agent, or Firm—Cushman, Darby & Cushman

[57] ABSTRACT

A polyhydroxyl monosulfoxide surfactant, usefully employed, for instance, in a cosmetic composition such as a shampoo, a hair dye formulation or a bath foam composition, has the formula

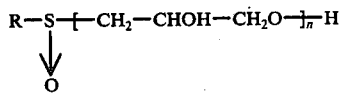

wherein R is selected from the group consisting of linear or branched aliphatic saturated or unsaturated hydrocarbon having 8–22 carbon atoms, alkylbenzyl having 8–22 carbon atoms and mixtures thereof, and $n$ has a statistical mean value greater than 1 and equal to or less than 10, and preferably 2–7.

16 Claims, No Drawings

POLYHYDROXYL MONOSULFOXIDE SHAMPOO COMPOSITIONS

This application is a division of application Ser. No. 563,459, filed Mar. 31, 1975, now U.S. Pat. No. 3,984,480, which is a continuation of application Ser. No. 372,103, filed June 21, 1973, now abandoned, which is a continuation-in-part of application Ser. No. 142,410, filed May 11, 1971, now abandoned.

The present invention relates to a new non-ionic surfactant which contains one or more polyhydroxyl monosulfoxides having the formula:

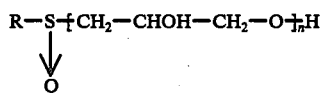
(I)

in which R is selected from the group consisting of a hydrocarbon group with 8 to 22 carbon atoms, the said hydrocarbon being linear or branched, saturated or unsaturated aliphatic, especially an alkyl, alkenyl or hydroxyalkyl group, or an alkylbenzyl group with 8 to 22 carbon atoms, or a mixture thereof; $n$ has a statistical mean value greater than 1 and equal to or less than 10, preferably between 2-7.

Polyhydroxyl monosulfoxides can be prepared by condensation of the glycidol of the formula

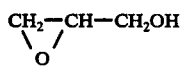
(II)

on aliphatic or aryl aliphatic mercaptan having the formula

 (III)

in which R has the same meaning as in formula (I) in the presence of alkaline catalysts, the addition of the glycidol being effected gradually. Initially, there is formed the monocondensate compound, and then a mixture of compounds of the general formula

 (V)

but for which the number of fixed glycidol molecules may be greater or less than the mean statistical value corresponding to the number of glycidol molecules used for one mercaptan molecule. As a result, for a value of $n$ greater than 1 there is obtained a mixture of compounds with different values for $n$, in other words, having longer or shorter hydrophilic chains, the whole of the $n$ values being distributed statistically about a mean value corresponding to the number of glycidol molecules used for one mercaptan molecule.

The molar proportions of glycidol used are a function of the degree of hydrosolubility that is desired. This solubility increases when $n$ is increased.

The polyhydroxyl thioethers that are obtained are then oxidized to sulfoxides, preferably by hydrogen peroxide.

As mercaptan of formula R—S—H there can be utilized either products that are available commercially or products obtained by standard synthesis processes such as condensation of alkaline hydrosulfides or thiourea on halides of the formula

RX (VI)

in which R has the meaning given in formula (I) and X is a halide, sulfurated hydrogen addition or thioacetic acid on alpha olefins or their oxides, or even by reduction of the corresponding sulfonic acids.

As alkaline catalysts there can be used alkaline hydroxides or alcoholates in molar proportions of 0.5 to 10%, preferably 4 to 8% with reference to the RSH mercaptan (III).

The monocondensation product is prepared first, i.e. the glycerol thioether indicated in the formula

 (IV)

in which R has the meaning indicated in formula (I), by addition to the R—S—H mercaptan preferably in an inert atmosphere, e.g., nitrogen, a molar equivalent of glycidol in the presence of one of the alkaline catalysts mentioned above, at a temperature of 20° to 80° C. The reaction is exothermal and the temperature at which the reaction mixture is held is essentially defined by the melting temperature of the glycerol thioether of formula (IV). The reaction is conducted just above this temperature in order to avoid any crystallization in the course of the reaction. The mixture is then heated to 120°-180° C, preferably 140°-160° C, at which temperature the rest of the glycidol is added that is necessary to attain the average $n$ degree of polymerization that is desired and to obtain the mixture of thioethers of the formula

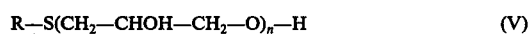 (V)

This addition must be effected dropwise with good agitation, and it can last from several minutes to several hours, preferably from ½ hour to 3 hours.

There is then obtained the compound or compounds of formula (I), by oxidizing the thioether of formula (IV) or the mixture of thioethers of formula (V) in a known way by addition of hydrogen peroxide, 30-35%, in stoichiometric quantity, at a temperature of 20°-50°, preferably 30°-35° C, possibly in the presence of 0.1 to 10% carboxylic acid with 1 to 4 carbon atoms.

Instead of starting with a mercaptan or a mixture of mercaptans of formula (III) it is possible directly to prepare the glycerol thioether of formula (IV) by standard procedures, e.g. by addition of the thioglycerol to the alpha olefins in ionic or radical catalysis, according to the invention to prepare essentially the branched or linear isomer; by condensation of thioglycerol on olefin oxides in the presence of basic catalysts, by condensation of thioglycerol on RX (VI) halides in an alkaline medium; by condensation in an alkaline medium or thioglycerol on a tosylate of the formula

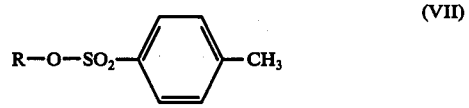 (VII)

or on a mesylate of formula

 (VIII)

In the mercaptans of formula (III) and the glycerol thioesters of formula (IV) which can be used as starting materials, R can designate a radical or a mixture of radicals such as octyl, decyl, dodecyl, tetradecyl, hexadecyl, octadecyl, eicosyl, 1-methyl-heptyl, 1-methyl-nonyl, 1-methyl-undecyl, 1-methyl tridecyl, 1-methyl-pentadecyl, 1-methyl-heptadecyl, 1-methyl-nonadecyl, 2-methyl-undecyl, 2-methyl-dodecyl, 2-methyl-tridecyl, 2-methyl-tetradecyl, 2-ethyl-hexyl, 2-octyl-dodecyl, oleyl, linoleyl, linolenyl, 2-hydroxy-dodecyl, 2-hydroxy-tridecyl, 2-hydroxy-tetradecyl, 2-hydroxy-pentadecyl, 2-hydroxy-hexadecyl, 2-hydroxy-heptadecyl, 2-hydroxy-octadecyl, dodecyl benzyl.

Properties and Applications

The non-ionic surfactants of the general formula (I) have the form of a clear yellow paste of more or less hard consistency, and their properties vary according to the length and nature of the lipophilic group and the polyoxyalkylene chain.

In a very general way, the hydrosolubility of these compounds is obtained with a mean degree of polymerization $n$ which is relatively low, even in the presence of electrolytes and at high temperatures. Thus, when R designates a normal dodecyl radical, with straight chain, the solubility in water of the compound of formula (I) is obtained for a value of $n$ that ranges between 2 and 2.5.

These compounds are characterized by a good foaming action. Thus for example the compounds of formula (I) for which R is an alkyl group with 12 to 14 carbon atoms and $n$ has a value of 2 to 3, are especially remarkable foaming agents, especially for non-ionic monosulfoxides customarily described as not foaming very much.

The compatibility of these new non-ionic surfactants with anionic compounds as well as with cationic compounds, taking into account the fact that they do not attack the ocular mucosa, makes it possible to use them in concentrations between 1 and 80%, preferably between 3 and 25% in shampoo compositions.

With lipophilic groups comprising a higher number of carbon atoms, e.g. 18, by varying the nature of the lipophilic group and parameter $n$, it is possible to prepare compounds of formula (I) which are good thickeners that can be used among other things in hair dye compositions, harmonizing agents, detergents, peptizers and emulsifiers.

The present invention thus relates also to cosmetic compositions, more especially shampoos, hair dyes, dispersions and emulsions characterized in that they contain at least one product of formula (I).

The present invention also relates to dispersions and emulsions, and especially to an "oil in water" emulsion as well as to a dispersion of an alkaline earth soap.

The "oil in water" emulsions can include from 10 to 50% oil, 5 to 20% emulsifier and 30 to 70% water.

As examples of polar oils, there can be listed esters of fatty acids such as isopropyl myristate or palmitate, ethyl palmitate, butyl stearate, 2-ethyl hexyl palmitate and isopropyl esters of fatty acids of lanolin, oils such as castor oil, sweet almond oil, olive oil and corn oil and solvents such as chlorobenzenes, 1,4-dichloro butane, monochloro butane, trichloroethylene and perchloroethylene.

The compositions, dispersions and emulsions can be stored in aerosol cans under pressure with conventional aerosol propellants such as monochlorotrifluoromethane or dichlorodifluoromethane. They can also include various adjuvants such as other surfactant compounds.

The compatibility of most of the compounds of formula (I) with aqueous solutions of alkaline hydroxides, e.g. with 40% NaOH, is one of their remarkable properties and permits their use in the textile industry, e.g. for mercerizing of cotton.

The polyhydroxyl non-ionic compounds of the present invention can also be utilized to disperse alkaline earth soaps, especially soaps of calcium and magnesium.

Per gram of soap to be dispersed there is used 0.02–1 g, preferably 0.1—0.2 g of the compounds of formula (I) in 100 ml solution with 400 ppm calcium chloride.

The test utilized to show this property is the one proposed by J. Alba Mendoza and C. Gomez Herrera at the 5th International Detergent Congress at Barcelona in 1968.

The following table shows, for certain compounds of formula (I) whose preparation is shown in the examples below, the minimal quantities Q (in milligrams) necessary for dispersion in the test conditions described by Alba Mendoza, of 50 mg sodium oleate in 50 ml water of hardness corresponding to a content of 400 ppm calcium chloride.

The sodium lauryl sulfate in the table was taken as control because it represents the medium type of dispersing agent for alkaline earth soaps.

| Compounds of Example | Q mg |
| --- | --- |
| 1 | $5<Q<10$ |
| 3 | $Q\leqq5$ |
| 6 | $5<Q<10$ |
| 7 | $3<Q<5$ |
| control: sodium lauryl sulfate | 68 |

EXAMPLE 1

Preparation of a mixture of compounds corresponding to general formula (I) in which R is the alkyl radical $C_{12}H_{25}$ and $n$ has a mean statistical value of 2.5.

To 630 g (3 moles) lauryl mercaptan there are added 28 g of a methanol solution of sodium methylate 4.6 meq/g (meq/g = milliequivalent/gram), and then in thirty minutes, under nitrogen atmosphere, 245 g glycidol (3 equivalents epoxide) at a temperature of 30° to 60° C. The temperature is then raised to 150° C, driving off the methanol, and then in the course of 1 hour and 40 minutes there are added, drop by drop, 369 g glycidol (4.5 equivalents). The temperature is held at 150° C for another 5 or 10 minutes after the end of the addition.

To 1,200 g of the product thus obtained there are added 6 ml acetic acid, and then at a temperature of 30° to 35° C, 248 ml hydrogen peroxide, to 11.65 moles/liter. The reaction is exothermal. The reaction mixture is held at a temperature below 40° C by cooling in a water bath.

The product is a lightly yellow paste, perfectly soluble in water and in 40% sodium hydroxide.

Its Kraft point for a 1% solution is 32° C. The turbidity point for a 0.5% solution is above 100° C in demineralized water, while its turbidity point is from 72 to 75° C in water that contains 10% NaCl.

Foam heights measured with the Ross-Miles apparatus for concentrations of 0.05%, 0.2% and 0.5% in hard water (corresponding to a content of 340 ml/l $CO_3Ca$) at 35° C are respectively 12.5 cm, 19 cm and 20 cm.

Tests with rabbits using an aqueous solution, 4.5% with a pH of 7, indicated absence of irritation to the mucosa of the eye.

EXAMPLE 2

Preparation of a mixture of compounds corresponding to the general formula (I) in which R is an alkyl radical with 14 carbon atoms and $n$ has a mean statistical value of 3.

In a first stage, mercaptan tetradecyl is prepared by addition of 30.5 g (0.37 mole) thioacetic acid to 68.2 g (0.35 mole) of corresponding alpha olefin, at 60° C, in the presence of 1 g azodiisobutyronitrile. The reaction is exothermal and the temperature reaches 70° C. The reaction mixture is held below this temperature for the whole duration of the addition, i.e. for 20 minutes. After ten minutes of additional agitation, the level of conversion is 97%.

There are then added, at 25° C, 70 g 40% NaOH and there is then gradual heating to 80° C. It is observed that at this temperature the reaction is clearly exothermal and that the reaction mass thickens.

The mercaptan is expanded by addition of 70 ml 6N hydrochloric acid.

The product is decanted and washed with 25 ml water to which 20 ml ether have been added to avoid formation of an emulsion.

The tetradecyl mercaptan thus obtained has a purity of 95%. To purify it, it is distilled at 165°–166° C under 14 mm Hg pressure. After distillation the tetradecyl mercaptan titers 4.15 meq/g in free SH groups.

To 36 g (0.15 mole) tetradecyl mercaptan prepared as indicated above, there are added, under nitrogen 2.25 ml of a methanol solution of sodium methylate, 4.6 meq/g, and then 12 g (0.15 equivalent) glycidol at 60° C. The addition takes 15 minutes.

The temperature is then raised to 150° C and in the course of 75 minutes there are added the remaining 24 g (0.3 equivalent) glycidol to reach the degree of polymerization $n = 3$. 35 g polyhydroxyl thioether are oxidized with 6.2 ml hydrogen peroxide, 130 volumes, in the presence of 0.2 ml acetic acid at 35° C.

The product has the form of a water soluble paste. Its Kraft point is 20° C for a 1% solution. Its turbidity point at 0.5% in demineralized water is above 100° C and 43° C in water that contains 10% NaCl.

The foam heights measured with the Ross-Miles apparatus at 35° C in hard water are respectively 12.5 cm, 16.5 cm and 19 cm for concentrations of 0.05%, 0.2% and 0.5%.

EXAMPLE 3

Preparation of a mixture of compounds corresponding to the general formula (I) in which R is a mixture of $C_{15}$–$C_{20}$ alkyl radicals from a mixture of $C_{15}$–$C_{20}$ olefins sold by Oronite Division, Chevron Chemicals, San Francisco, Calif. (U.S.A.) and $n$ has a mean statistical value of 4.

The corresponding mercaptan is prepared as in Example 2 by addition of 35 g thioacetic acid, at 70° C, to 93 g of the mixture of $C_{15}$–$C_{20}$ olefins, in the presence of 1 g azodiisobutyronitrile. After 1 hour 30 minutes at 70°–80° C the temperature of the mixture is raised to 95°–100° C and this temperature is held for 30 minutes giving a yield that is almost quantitative.

There are then added in the course of 10 minutes, 80 g of 40% NaOH at 60° C in the presence of 20 ml 96° ethyl alcohol. The mixture is heated under reflux for about 30 minutes until a suitable level of hydrolysis is reached.

There is then produced cold acidification by 6 N hydrochloric acid and the mercaptan mixture is salted out. After drying the mixture presents a titer of 3.2 meq/g free SH.

To 50 g of this mixture there are added 2.4 ml sodium methylate in solution in methanol, and in the course of 30 minutes, 12.5 g glycidol at 60° C. The mixture is then heated to 150° C and there are then added dropwise in the course of 1 hour and 30 minutes, 37 g glycidol, which makes as a total 4 equivalents glycidol per equivalent of mercaptan.

The thioether is oxidized with the stoichiometric quantity of hydrogen peroxide in the presence of 0.5% acetic acid.

The mixture of polyhydroxyl sulfoxides obtained has the form of a rather hard water soluble paste, which is also soluble in 40% NaOH. Its Kraft point is 47° C. Its turbidity point is above 100° C in demineralized water and in water that contains 10% NaCl.

EXAMPLE 4

Preparation of a mixture of compounds corresponding to the general formula (I) in which R is the octadecyl radical and $n$ represents the mean statistical value of 4.

The octadecyl mercaptan is prepared by heating at reflux for 5 hours in absolute ethyl alcohol stoichiometric quantities of octadecyl bromide and thiourea.

After having driven off the major part of the alcohol, the reaction mixture is hydrolyzed with 20% NaOH possibly with addition of water if the medium is too thick. By heating the reaction mixture to 70° C, a separation into two phases is effected.

After drying of the organic phase, the octadecyl mercaptan is precipitated by absolute ethyl alcohol.

The octadecyl mercaptan is then condensed with 4 moles glycidol per mole octadecyl mercaptan, by first introducing a first molar equivalent of glycidol to obtain 3-octadecylthio-propane-1,2 diol at 80° C, the rest of the glycidol then being introduced at 155° C in the course of 2 hours 20 minutes.

The obtained thioether is a rather consistent wax, so that oxidation is effected in acetone, at 35°–40° C.

The precipitated sulfoxide has the form of a white powder that is soluble in water with a slight opalescence. It is also soluble in a concentrated solution of sodium hydroxide (NaOH 40%).

It Kraft point is from 58° to 60° C. Its turbidity point is above 100° C in demineralized water and in water that contains 10% NaCl.

This mixture of compounds constitutes a good emulsifier for oil and water, leading to a stable emulsion.

EXAMPLE 5

Preparation of a mixture of compounds corresponding to the general formula (I) in which R is a mixture of straight chain and branched alkyl radicals of which about 14% are 2-methyl alkyl, derived from a mixture of synthesized $C_{12}$–$C_{15}$ aliphatic alcohols sold by SHELL Company as Dobanol 25, in which formula $n$ has a mean statistical value of 3.5.

In a first stage the alkylthioethers of glycerol are prepared by reaction of the mixture of corresponding alcohols with methane sulfochloride, with subsequent condensation with thioglycerol in an alkaline medium.

205 g (1 mole) Dobanol 25 are mixed with 101 g triethylamine in 250 ml benzene and in the course of 90 minutes there are introduced, at 30°–40° C, 114 g (1 mole) methane sulfochloride. After another hour of agitation, the level of reaction is 97.5%.

After filtration of the triethylamine hydrochloride, the stoichiometric amount of the sodium derivative of thioglycerol is added in nitrogen atmosphere. The mixture is brought to 100° C, partly eliminating the benzene and adding in the course of reaction 30 ml methanol to avoid thickening of the reaction mass.

The alkyl thioglycerol is then expanded with 100 ml water, decanted and then dried under vacuum to 100° C.

To 65 g (0.2 mole) of the product thus obtained there are added 2 ml of methanol solution of sodium methylate, 4.6 meq/g. The reaction mixture is then heated to 155° C and there is introduced therein, drop by drop, in the course of 90 minutes, 0.5 mole glycidol.

After oxidation with the stoichiometric quantity of hydrogen peroxide in the presence of 0.5% acetic acid, a water soluble product is obtained.

Its Kraft point at 1% is 19° C. Its turbidity point at 0.5% is 80° C in demineralized water and 68° C in water that contains 10% NaCl.

Foam heights measured with the Ross-Miles apparatus at 35° C in hard water are respectively 10.5 cm, 16.5 cm and 18 cm for concentrations of 0.05%, 0.2% and 0.5%.

EXAMPLE 6

Preparation of a mixture of compounds substantially identical with that of Example 5, but with a mean degree of polymerization of 4 ($n = 4$). This slight increase of the value of $n$ has the result of an increase in the range of solubility, i.e. a lowering of the Kraft point to 8° C and an elevation of the turbidity points in demineralized water (>100° C) and in water containing 10% NaCl (85° C).

Foam heights, which were little changed, are respectively 10.5 cm, 15.5 cm and 18.5 cm.

EXAMPLE 7

Preparation of a mixture of compounds corresponding to the general formula in which $n$ has an average statistical value of 6 and R is the oleyl radical (this is the derived hydrocarbon radical of oleic acid).

To 78 g (0.3 mole) oleyl alcohol and 30 g triethylamine in 40 ml benzene, there are added at ordinary temperature in the course of 75 miinutes, 34 g methane sulfochloride. After a night at ordinary temperature, the reaction is total. The triethylamine salt that is formed is filtered off and the sodium derivative of thioglycerol is added at 40° C. The benzene is partly driven off and 50 ml methanol are added. After agitation for 2½ to 3 hours, at 40°–45° C, the level of reaction is 95%.

The thioether formed is salted out with 50 ml water at 70° C and dehydrated under vacuum at 95° C.

The theoretical quantity of glycidol is added at 155° C to have a statistical mean of 6 units, —CH$_2$—CHOH—CH$_2$O—, per fatty chain. After oxidation with hydrogen peroxide there is obtained a brown paste soluble in water and in 40% NaOH.

The Kraft point is below 0° C and the turbidity point is above 100° C in demineralized water as well as in water containing 10% NaCl.

Foam heights measured with the Ross-Miles apparatus are respectively 5.5 cm, 11.5 cm and 13.5 cm for concentrations of 0.05%, 0.2% and 0.5%.

EXAMPLE 8

Preparation of a mixture of compounds of the general formula (I) in which R is the dodecyl benzyl radical and $n$ represents a mean statistical value of 4.5.

First there is prepared dodecylbenzylmercaptan by reflux heating for 7 hours of 42.5 g dodecylbenzyl chloride with 11 g of thiourea in 100 ml absolute ethyl alcohol.

After addition of 50 l ml water, the isothiouronium salt is hydrolyzed with 20% NaOH. The organic phase is decanted. After drying the obtained mercaptan titers 84% thiol groups.

Purification is effected by precipitation in absolute ethyl alcohol of the cadmium salt of mercaptan obtained from crystallized cadmium acetate. The mercaptan is then regenerated by 6N HCl. After drying and distillation at 145°–150° C/0.1 mm Hg, the product titers 3.4 meq/g of free SH groups (theoretical value 3.42 meq/g).

To 17.5 g (0.06 mole) dodecylbenzyl mercaptan thus obtained there are added 0.9 ml sodium methylate, then 4.8 g glycidol at 60° C and then 16.5 g glycidol at 155° C, for a total of 0.27 equivalent glycidol.

After oxidation in hydrogen peroxide, in the presence of 0.5% acetic acid, there is obtained the desired water soluble product.

Its Kraft point is 75° C and its turbidity point is above 100° C in demineralized water.

EXAMPLE 9

Preparation of a mixture of compounds corresponding to the general formula (I) in which R is a mixture of 2-hydroxy alkyl radicals with 11 to 14 carbon atoms, $n$ having the mean statistical value of 3.

To 21.5 g (0.2 mole) thioglycerol there are added 1.9 g methanol solution of sodium methylate (0.01 mole) and then in a nitrogen atmosphere at 80°–85° C, 43 g (0.2 equivalent) of a mixture of 1,2-epoxy alkylenes having 11 to 14 carbon atoms and sold as NEDOX 1114 by the ARCHER DANIELS MIDLAND Company. The reaction is exothermal and the duration of the introduction is 20 minutes. Conversion is substantially quantitative.

The mixture is then heated to 155° C and in the course of 1 hour there are introduced 32 g glycidol (0.4 equivalent). After cooling there are added to 48 g (0.1 mole) of the mixture thus obtained 0.3 ml acetic acid and then, drop by drop, 9.1 ml hydrogen peroxide to 123 volumes while maintaining the temperature between 30° and 35° C.

There is thus obtained a clear beige water soluble cream.

Its Kraft point is 50°–51° C for a 1% solution. The turbidity point at a concentration of 0.5% is above 100° C in demineralized water and in water that contains 10% NaCl.

Foam heights measured with the Ross-Miles apparatus, for concentrations of 0.05%, 0.2% and 0.5% are, at 50° C, respectively 12.5 cm, 18.5 cm and 19 cm.

| EXAMPLE 10 - Non-ionic shampoo | |
| --- | --- |
| Compounds obtained as in Example 1 | 15 g |
| Lauryl diethanolamide | 2 g |
| Carboxymethyl cellulose | 0.3 g |
| Water, q.s.p. | 100 g |

This composition has the form of a clear solution with a pH of 7. On application to the hair, a very abundant foam is rapidly obtained.

| EXAMPLE 11 - Cationic shampoo | |
|---|---|
| Compounds as in Example 1 | 7 g |
| Dimethyl hydroxyethyl cetyl ammonium bromide | 3 g |
| Hydroxypropyl methyl cellulose | 0.25 g |
| Lactic acid, q.s.p. | pH 3 |
| Water, q.s.p. | 100 g |

A clear solution is obtained. The presence of the compounds prepared as in Example 1 promote formation of the foam and allow easier rinsing of the hair. Besides, the hair is easier to untangle than is hair washed with a present day cationic composition.

| EXAMPLE 12 - Cationic shampoo | |
|---|---|
| Compounds obtained as in Example 2 | 8 g |
| Dimethyl hydroxyethyl cetyl ammonium bromide | 3.5 g |
| Hydroxypropyl methyl cellulose | 0.3 g |
| Lactic acid, q.s.p. | pH 3 |
| Water, q.s.p. | 100 g |

A foamable clear solution is obtained. Hair washed with this solution is easy to untangle.

| EXAMPLE 13 - Baby shampoo | |
|---|---|
| Compounds obtained as in Example 1 $$R-NH-CH-COONa$$ $$\quad\quad\quad\;\, \vert$$ $$\quad\quad CH_2-CONH-(CH_2)_3-N\begin{array}{c}\diagup C_2H_5\\ \diagdown C_2H_5\end{array}$$ (R: hydrocarbon radical of fatty acids of copra) | 5 g |
| Hydroxyethylene lauryl alcohol with 12 moles ethylene oxide per mole alcohol | 3 g |
| | 5 g |
| Lauryl diethanolamide | 1.5 g |
| Lactic acid, q.s.p. | pH 5 |
| Water, q.s.p. | 100 g |

This composition has the form of a clear solution.

| EXAMPLE 14 - Baby shampoo | |
|---|---|
| Compounds obtained as in Example 1 | 8 g |
| MIRANOL C2M, having the formula $$C_{11}H_{23}-C\begin{array}{c}\diagup HO\\ \diagdown\\ \Vert\\ N\end{array}\begin{array}{c}CH_2-COONa\\ \diagup\\ N\\ \diagdown CH_2\\ \diagup\\ CH_2\end{array}\begin{array}{c}\\ \\ CH_2-CH_2-O-CH_2-COONa\\ \\ \end{array}$$ | 20 g |
| LAUTROL AW5 (MALSTROM) (hydroxyethylene lanolin alcohols with 75 moles ethylene oxide | 0.3 g |
| Hydroxypropylethyl cellulose | 0.3 g |
| Lactic acid, q.s.p. | pH 8 |
| Water, q.s.p. | 100 g |

This composition has the form of an opaque solution, has good foaming characteristics and is suitable as a baby shampoo.

| EXAMPLE 15 - Anionic shampoo | |
|---|---|
| Compounds obtained as in Example 1 | 10 g |
| MAYPON 4 CT (MAYWOOD)*Product of condensation of fatty acids of coprah on polypeptides | |
| MAYPON UD (MAYWOOD)*Product of condensation of undecylenic acid on protein hydrolysis products | 30 g |
| | 5 g |
| Carboxymethyl cellulose | 0.4 g |
| Water, q.s.p. | 100 g |

This composition has the form of a clear solution with a pH of 7.

| EXAMPLE 16 - Cationic shampoo cream | |
|---|---|
| Dimethyl hydroxyethyl cetyl ammonium bromide | 3 g |
| N-lauryl beta-imino sodium propionate | 5 g |
| Hydroxyethylene lauryl alcohol, 12 moles ethylene oxide per mole alcohol | 15 g |
| Lauryl diethanolamide | 4 g |
| Compounds obtained according to Example 4 | 12 g |
| Glycerol monostearate | 2.5 g |
| Lactic acid, q.s.p. | pH 3 |
| Water, q.s.p. | 100 g |

*Maywood Division of STEPAN CHEMICALS, New Jersey (N.J.) U.S.A.

The thickening to a cream is effected by use of the compounds prepared as in Example 4.

| EXAMPLE 17 - Cationic shampoo with pearly glints | |
|---|---|
| Dimethyl hydroxyethyl cetyl ammonium bromide | 2 g |
| $$R-NH-CH-COONa$$ $$\quad\quad\quad\;\, \vert$$ $$\quad\quad CH_2-CONH-(CH_2)_3-N\begin{array}{c}\diagup C_2H_5\\ \diagdown C_2H_5\end{array}$$ R = hydrocarbon radical of fatty acids of copra | 3 g |
| Non-ionic compounds of the formula $C_{12}H_{25}-O-[-C_2H_3O(CH_2OH)-]_{1.2}H$ | 10 g |
| Compounds prepared as in Example 4 | 6 g |
| Ethyl cellulose | 0.25 g |
| Lactic acid, q.s.p. | pH 5 |
| Water, q.s.p. | 100 g |

This composition is a clear solution.

| EXAMPLE 18 - Baby shampoo | |
|---|---|
| $$R-NH-CH-COONa$$ $$\quad\quad\quad\;\, \vert$$ $$\quad\quad CH_2-CONH-(CH_2)_3-N\begin{array}{c}\diagup C_2H_5\\ \diagdown C_2H_5\end{array}$$ R = hydrocarbon radical of fatty acid of copra | 3 g |
| MIRANOL C2M of the formula $$C_{11}H_{23}-C\begin{array}{c}\diagup HO\\ \diagdown\\ \Vert\\ N\end{array}\begin{array}{c}CH_2-COONa\\ \diagup\\ N\\ \diagdown CH_2\\ \diagup\\ CH_2\end{array}\begin{array}{c}\\ \\ CH_2-CH_2-O-CH_2-COONa\\ \\ \end{array}$$ | 30 g |
| Oxyethylenated lauryl alcohol with 12 moles ethylene oxide | 15 g |
| Compounds as in Example 4 | 8 g |
| Monoethanolamine of copra | 1 g |
| Water, q.s.p. | 100 g |
| Lactic acid, q.s.p. | pH 8 |

This composition has the form of a clear solution.

| EXAMPLE 19 - Dye shampoo (foaming) | |
|---|---|
| Compounds as in Example 1 | 10 g |
| Nonylphenol oxyethylenated with 4 moles ethylene oxide | 35 g |
| Ethyl alcohol, 96° | 13 g |
| Propylene glycol | 5 g |
| Ammonia, 22° Be' | 12 ml |
| Dyes: | |
| Resorcinol | 0.040 g |
| Meta aminophenol base | 0.060 g |
| Paraaminophenol base | 0.280 g |
| Nitro paraphenylene diamine | 0.020 g |
| Para toluylene diamine | 0.120 g |
| Hydroquinone | 0.170 g |
| Sodium salt of ethylene diamine tetraacetic acid | 3 g |
| Sodium bisulfite d = 1 | 0.800 ml |
| Water, q.s.p. | 100 g |
| pH = 9.5 | |

There are mixed, in a plastic applicator, 50 grams of the above composition with the same amount of hydrogen peroxide, at 20 volumes, and the gel that is obtained is applied to light chestnut hair, using the applicator. It is distributed by shampooing until a foam is obtained. The composition is allowed to act for 30 minutes. The hair is then rinsed and dried and a golden blond shade superimposed to the light chestnut color of the hair is obtained.

| EXAMPLE 20 - Cream dye (thickening) | |
|---|---|
| Composition as in Example 4 | 10 g |
| Cetyl stearyl alcohol | 20 g |
| Cetyl stearyl sodium sulfate | 5 g |
| Ammonia, 22° Bé | 10 ml |
| Dyes: | |
| Metadiaminoanisol sulfate | 0.048 g |
| Resorcinol | 0.420 g |
| Meta aminophenol base | 0.150 g |
| Paraaminophenol base | 0.035 g |
| Nitro paraphenylene diamine | 0.004 g |
| Paratoluylene diamine | 1 g |
| Sodium salt of ethylene diamine tetraacetic acid | 1 g |
| Sodium bisulfite d = 1.32 | 1.2 ml |
| Water, q.s.p. | 100 g |
| pH = 9.7. | |

30 grams of the above creamy composition are mixed with 45 g hydrogen peroxide at 20 volumes. There is obtained a cream of smooth consistency that is agreeable to use and that, when applied with a small brush, adheres well to the hair. It is allowed to remain on the hair for 30 minutes. The hair is then rinsed and dried. On 100% white hair, a blond hue is obtained.

| EXAMPLe 21 - "Oil in water" emulsion | |
|---|---|
| Mixture of compounds obtained as in Example 4 | 10 g |
| Peanut oil | 30 g |
| Water | 60 g |
| Total: | 100 g |

The emulsion thus obtained constitutes a cream which has good stability.

| EXAMPLE 22 - "Oil in water" emulsion | |
|---|---|
| Mixture of the compounds obtained as in Example 4 | 10 g |
| Isopropyl myristate | 30 g |
| Water | 60 g |
| Total: | 100 g |

The emulsion thus obtained constitutes a cream with good stability.

| EXAMPLE 23 - "Oil in water" emulsion | |
|---|---|
| Mixture of the compounds prepared as in Example 4 | 20 g |
| Chlorobenzene | 30 g |
| Water | 50 g |
| Total: | 100 g |

A cream with good stability is obtained.

EXAMPLE 24

Preparation of a mixture of compounds corresponding to general formula (I) in which R is the alkyl radical $C_8H_{17}$ and $n$ has a mean statistical value of 1.5.

To 29 g (0.2 mole) octyl mercaptan there are added 2 g of a methanol solution of sodium methylate 4.9 meq/g, and then in thirty minutes, under nitrogen atmosphere, 15 g glycidol (0.2 equivalents epoxide) at temperature of 40° C. The temperature is then raised to 150° C, driving off the methanol, and then in the course of 45 minutes there are added, drop by drop, 7.4 g glycidol (0.1 equivalent). The temperature is held at 150° C for another 5 or 10 minutes after the end of the addition.

To the product thus obtained there are added 1 ml acetic acid, and then at a temperature of 30° to 35° C, 16 ml hydrogen peroxide, 12.5 moles/liter. The reaction is exothermal. The reaction mixture is held at a temperature below 40° C by cooling in a water bath.

The product is perfectly soluble in water.

EXAMPLE 25

Preparation of a mixture of compounds corresponding to the general formula (I) in which R is a mixture of 2-hydroxy alkyl radicals with 15 to 18 carbon atoms, $n$ having the mean statistical value of 10.

To 5.4 g (0.05 mole) thioglycerol there are added 0.7 g methanol solution of sodium methylate (4.9 meq/g) and then in a nitrogen atmosphere at 80°-85° C, 12.6 g (0.05 equivalent) of a mixture of 1,2-epoxy alkylenes having 15 to 18 carbon atoms and sold as NEDOX 1518 by the ARCHER DANIELS MIDLAND Company. The reaction is exothermal and the duration of the introduction is 10 minutes. Conversion is substantially quantitative.

The mixture is then heated to 155° C and in the course of 1 hour 30 minutes there are introduced 33.3 g glycidol (0.45 equivalent). After cooling, 25.5 g of the mixture thus obtained are dissolved in 20 ml water and 2.55 ml acetic acid are then added (10% of the product) and then drop by drop, 2.0 ml hydrogen peroxide at 137 volumes while maintaining the temperature between 30° and 35° C.

The product thus obtained is soluble in water and in NaOH 40%.

| EXAMPLE 26 - Lather bath | |
|---|---|
| Compound of formula (I) as in Example 2 | 10 g |
| Sodium sulfate of dodecyltetradecylether oxyethylenated with 2.2 moles ethylene oxide | 15 g |
| Diethanolamide of copra | 5 g |
| Hydroxypropylmethylcellulose | 2 g |
| Lactic acid q.s.p. pH 6.5 | |
| Water, q.s.p. | 100 g |

This composition is a clear viscous liquid.

15 to 20 g of this composition diluted in a water bath i.e. 100-150 liters of water, produce a very important volume of lather. This lather is characterized by the fact that it is thick, consistent, stable, very pleasant to use and that is does not break down when soap is used, as the calcium and magnesium salts present in hard water are dispersed by the compound of formula (I).

EXAMPLE 27

| Compound of Example 4 | 10 g |
|---|---|
| 1,4-dichlorobutane | 30 g |
| Water | 60 g |

The compound prepared in accordance with Example 4 is admixed with water at 70° C. To this mixture there is then added, at this temperature and with good agitation, the above chlorinated derivative to produce a good emulsion which on cooling provides a very thick milk.

EXAMPLE 28

| Compound of Example 3 | 10 g |
|---|---|
| n-butyl chloride | 27 g |
| Water | 63 g |

The compound prepared in accordance with Example 3 is admixed with water at 40° C. To this mixture there is then added, with agitation, the said n-butyl chloride, thereby providing a good emulsion.

EXAMPLE 29

| Compound of Example 7 | 10 g |
|---|---|
| n-butyl chloride | 30 g |
| Water | 60 g |

The compound prepared in accordance with Example 7 is admixed with water at 40° C. To this mixture there is then added, with agitation, the said n-butyl chloride, thereby providing a good emulsion.

What is claimed is:

1. A composition for use as a shampoo or foamable bath composition comprising an aqueous solution of at least one compound having the formula

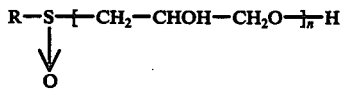

wherein R is selected from the group consisting of linear or branched, saturated or unsaturated hydrocarbon having 8 to 22 carbon atoms, alkylbenzyl having 8 to 22 carbon atoms, and a mixture thereof, and $n$ has a statistical mean value of 2 to 10, said compound being present in an amount of 1 to 80 percent by weight of said composition.

2. The composition of claim 1 wherein R is alkyl.

3. The composition of claim 1 wherein R is alkenyl.

4. The composition of claim 1 wherein R is hydroxyalkyl.

5. The composition of claim 1 wherein R is alkylbenzyl containing 8 to 22 carbon atoms.

6. The composition of claim 1 wherein R is 2-hydroxyalkyl.

7. The composition of claim 1 wherein $n$ is 2-7.

8. The composition of claim 1 wherein $n$ is 1.5.

9. In an emulsion composition, the improvement comprising, as the emulsifying agent therefor, at least one compound having the formula

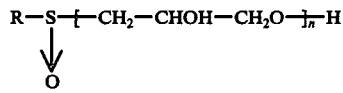

wherein R is selected from the group consisting of linear or branched, saturated or unsaturated, hydrocarbon having 8 to 22 carbon atoms, alkylbenzyl having 8 to 22 carbon atoms, and a mixture thereof, and $n$ has a statistical mean value of 2 to 10, said emulsifying agent being present in an amount of 1 to 80 percent by weight of said emulsion.

10. The emulsion of claim 9 wherein said emulsifying agent is present in an amount between 3 and 25 percent by weight thereof.

11. An oil-in-water emulsion comprising 10-50 weight percent oil, 5-20 weight percent emulsifying agent and 30-70 weight percent water, said emulsifying agent comprising at least one compound having the formula

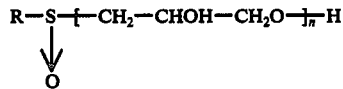

wherein R is selected from the group consisting of linear or branched, saturated or unsaturated, hydrocarbon having 8 to 22 carbon atoms, alkylbenzyl having 8 to 22 carbon atoms, and a mixture thereof, and $n$ has a statistical mean value of 2 to 10.

12. The oil-in-water emulsion of claim 11 wherein said oil is a polar oil.

13. The oil-in-water emulsion of claim 12 wherein said polar oil is a triglyceride.

14. The oil-in-water emulsion of claim 12 wherein said polar oil is an ester of a fatty acid.

15. The oil-in-water emulsion of claim 12 wherein said polar oil is a chlorinated solvent.

16. The oil-in-water emulsion of claim 15 wherein said chlorinated solvent is selected from chlorobenzene, 1,4-dichloro butane, monochloro butane, trichloroethylene and perchloroethylene.

* * * * *